(12) United States Patent
Gerlach et al.

(10) Patent No.: US 10,792,148 B2
(45) Date of Patent: Oct. 6, 2020

(54) INTRAOCULAR LENS WITH SINGLE LENS TELESCOPE INTEGRATED IN THE OPTICAL PART THEREOF

(71) Applicant: Carl Zeiss Meditec AG, Jena (DE)

(72) Inventors: Mario Gerlach, Glienicke-Nordbahn (DE); Werner Fiala, Vienna (AT)

(73) Assignee: Carl Zeiss Meditec AG, Jena (DE)

( * ) Notice: Subject to any disclaimer, the term of this patent is extended or adjusted under 35 U.S.C. 154(b) by 164 days.

(21) Appl. No.: 15/625,419

(22) Filed: Jun. 16, 2017

(65) Prior Publication Data

US 2017/0281335 A1  Oct. 5, 2017

Related U.S. Application Data

(63) Continuation of application No. PCT/EP2015/080314, filed on Dec. 17, 2015.

(30) Foreign Application Priority Data

Dec. 18, 2014 (DE) .......................... 10 2014 119 010

(51) Int. Cl.
*A61F 2/16* (2006.01)
(52) U.S. Cl.
CPC .... *A61F 2/1651* (2015.04); *A61F 2002/1683* (2013.01); *A61F 2002/1689* (2013.01); *A61F 2250/0053* (2013.01)
(58) Field of Classification Search
CPC .................. A61F 2/1648; A61F 2/1651; A61F 2250/0053; A61F 2230/0093; A61F 2250/0065; A61F 2250/0091

USPC .......................................................... 623/6.34
See application file for complete search history.

(56) References Cited

U.S. PATENT DOCUMENTS

| | | | |
|---|---|---|---|
| 4,666,446 A | 5/1987 | Koziol et al. | |
| 5,391,202 A | 2/1995 | Lipshitz et al. | |
| 5,814,103 A | 9/1998 | Lipshitz et al. | |
| 6,066,171 A | 5/2000 | Lipshitz et al. | |
| 6,596,026 B1 * | 7/2003 | Gross .................... | A61F 2/1648 623/6.25 |
| 8,579,970 B1 | 11/2013 | Zadno-Azizi et al. | |

(Continued)

FOREIGN PATENT DOCUMENTS

| | | | |
|---|---|---|---|
| DE | 69431428 T2 | 6/2003 | |
| DE | 69921648 T2 | 11/2005 | |

(Continued)

OTHER PUBLICATIONS

International Search Report dated Mar. 21, 2016 of international application PCT/EP2015/080314 on which this application is based.

(Continued)

*Primary Examiner* — Paul B Prebilic
(74) *Attorney, Agent, or Firm* — Falk Ewers; Ewers IP Law PLLC (57) ABSTRACT

An intraocular lens is provided. The intraocular lens includes an optical part and an adjoining haptic part. The optical part includes an optically imaging element and a telescope, the entire telescope being integrally formed and being integrated in the optical imaging element. The optically imaging element has a convexly-curved front side and a concavely-curved rear side. Further, the optically imaging element is arranged as a single lens system.

9 Claims, 5 Drawing Sheets

(56) References Cited

U.S. PATENT DOCUMENTS

| | | | |
|---|---|---|---|
| 9,622,852 B2 | | 4/2017 | Simonov et al. |
| 2004/0082995 A1* | | 4/2004 | Woods .................. A61F 2/1648 623/6.34 |
| 2005/0071002 A1* | | 3/2005 | Glazier ................. A61F 2/1613 623/6.13 |
| 2005/0288784 A1* | | 12/2005 | Peyman ................ A61F 2/1648 623/6.35 |
| 2011/0040376 A1* | | 2/2011 | Christie .................... A61F 2/15 623/6.17 |

FOREIGN PATENT DOCUMENTS

| | | |
|---|---|---|
| DE | 112010004191 T5 | 11/2012 |
| EP | 0897702 A2 | 2/1999 |
| EP | 1818023 A1 | 8/2007 |
| FR | 1103399 | 11/1955 |

OTHER PUBLICATIONS

Written Opinion of the International Searching Authority in PCT/EP2015/080314 (from which this application claims priority) dated Mar. 21, 2016 and English-language translation thereof.

* cited by examiner

INTRAOCULAR LENS WITH SINGLE LENS TELESCOPE INTEGRATED IN THE OPTICAL PART THEREOF

CROSS REFERENCE TO RELATED APPLICATIONS

This application is a continuation application of international patent application PCT/EP2015/080314, filed Dec. 17, 2015, designating the United States and claiming priority to German application 10 2014 119 010.6, filed Dec. 18, 2014, and the entire content of both applications is incorporated herein by reference.

TECHNICAL FIELD

The invention relates to an intraocular lens including an optical part and an adjoining haptic part. The optical part includes an optically imaging element and a telescope.

BACKGROUND

The human eye may be afflicted by very different visual defects on account of its relatively complex structure and hence also, in particular, on account of the parts provided for optical imaging and/or other influencing factors. Individually, these may be differently pronounced in terms of strength; on the other hand, a plurality of different visual defects also may be present in an eye.

Eye lenses for correcting visual defects are known in the form of intraocular lenses with multifaceted configurations.

By way of example, such an intraocular lens is known from U.S. Pat. No. 5,391,202. Intraocular lenses including a telescope extend a visual field of a patient suffering from a degeneration of the macula. In the case of macular degeneration, the affected persons are unable to read without special telescopic or microscopic spectacles which produce a magnification of the object on the retina and hence on the macula.

However, the structure is very complex in the known intraocular lens and it is difficult to produce said intraocular lens. This is because the intraocular lens requires a plurality of separate parts; namely, firstly, a body element which may have a biconvex or plano-convex configuration. Centrally in the middle, this body element has a continuous bore, in which separate lens elements of the telescope, arranged at a distance from one another, are positioned. Provision may be made for the lens element to have an integral embodiment with the body element. However, the second lens element must necessarily be provided as a separate part in all cases since a gas filling must be introduced into a cavity between the two lens elements and since, necessarily, such a cavity must also be formed. As a result of this configuration, the positioning of the two convex lenses in relation to one another is very difficult and not possible with a permanently secured position. As a result, unwanted imaging properties of the telescope formed from a plurality of separate lenses may emerge and hence the intraocular lens may only provide limited improvement in view of its specific functionality for adapting the visual range of a patient with macular degeneration.

An intraocular lens which likewise includes a telescope is known from U.S. Pat. No. 9,622,852. Two separate lens elements for constructing the telescope are also provided there in a mandatory fashion, said two separate lens elements being connected by way of connection elements in order to be able to facilitate a relative movability of the two lens elements of the telescope. This configuration also has a very complex structure and it is difficult to produce, and as a result, a limited functionality in view of the visual field design for a patient with macular degeneration also occurs in this case.

Moreover, U.S. Pat. No. 6,066,171 describes an intraocular lens with a swivelable telescope. In view of the complexity, the structure therein exceeds the embodiments as specified in the two aforementioned documents of the related art.

In addition, the respective thickness, in particular the central thickness of the intraocular lens, is very large in all embodiments and the intraocular lens as such is relatively rigid on account of the configuration. This has a significant disadvantage because it can only be folded to a relatively qualified extent and therefore it is unsuitable for an implantation, which is suitable for a small incision, into the eye. Therefore, the implantation into an eye, in particular into a capsular bag, is linked to relatively large incisions in the case of such known lenses which, in turn, is also disadvantageous for the patient.

Moreover, the optical part is formed by the telescope in the two known intraocular lenses mentioned above. This has substantial disadvantages in view of the further vision of the patient in the case of specific imaging of the incident light. Additionally, the field of vision is restricted in any case by the holding mechanism or by the carriers, which respectively hold this telescope, in these known intraocular lenses as these required carriers do not contribute to the optical imaging.

SUMMARY

It is an object of the present invention to provide an eye lens by which the visual defect AMD (age-related macular degeneration) may be corrected in an improved manner.

The object is achieved by providing an intraocular eye lens having an optical part including an optically imaging element and a telescope and a haptic part connected to the optical part. The telescope has an integral embodiment, i.e., is formed in one piece, is integrated into the optically imaging element, has a convexly-curved front side and a concavely-curved rear side, and is a convex-concave telescope arranged as a single lens system. The convexly-curved front side of the telescope has a convex curvature and faces towards incident light entering the intraocular lens. The concavely-curved rear side of the telescope has a concave curvature and faces away from the incident light.

An intraocular lens according to an aspect of the invention includes an optical part and an adjoining optically ineffective haptic part. The optical part, and hence an imaging part acting in an optically defined manner, includes an optically imaging element and a telescope. This means that at least two different optically effective components are present in this case. Therefore, within the context of the invention, this should not be understood to mean that the telescope is also the entire optically imaging element at the same time.

According to an aspect of the invention, the telescope is a complete or entire telescope having an integral embodiment and being integrated into the optically imaging element. This means that, therefore, the entire telescope is also embodied in integral fashion with the optically imaging element and also preferably produced in an integral fashion with the optically imaging element. Hence, the optical part of this intraocular lens is embodied with two separate optically effective components, in particular components with different optical effects. The components, however, are produced and provided in a common composite. This integral configuration is such that the optically imaging element and the telescope are not overlaid but embodied adjacent to one another and hence embodied lying next to one another and each image with an individual optical effect.

This intraocular lens according to an aspect of the invention is embodied to adapt the visual field and hence, in particular, to extend a visual field in the case of macular degeneration. This specific design of the optical part substantially improves this visual field adaptation in comparison with intraocular lenses from the related art. By way of example, this is also due to the fact that the complexity of the structure is reduced as the telescope and the optically imaging element have an integral embodiment. Unwanted position tolerances between individual lens elements of a telescope, as they occur in the related art, no longer occur in the intraocular lens according to the aspect of the invention, and thus, it is precisely the imaging property of the telescope which is improved to a particular extent in relation to the embodiments in the related art. As a result of the additional configuration with the optically imaging element, an additional function in view of the optical effect of the optical part is complemented beyond the optical imaging properties of the telescope and hence the entire optical imaging of the intraocular lens is improved, in particular in the case of macular degeneration. By virtue of a position fixation being formed according to an aspect of the invention between the entire telescope and the optically imaging element by the integration of these components, it is also possible to avoid unwanted position tolerances and hence also disadvantageous effects of the respective imaging properties of the individual components, both on their own and with an operative connection.

As a result of the integral construction of telescope and optically imaging element, the intraocular lens obtains a relatively low flexural rigidity, which is particularly advantageous for an implantation, and which is suitable for a small incision into an eye.

In particular, a telescope is an element through which distant objects are seen with a larger field of view than with the free eye and are therefore seen as if they are brought closer. The focal length of the convex side of the telescope is greater than the focal length of the concave side. As a result, a telescope also differs substantially from a convex-concave lens.

In particular, provision is made for the telescope to be situated centrally in the middle in a direction perpendicular to an optical main axis of the intraocular lens and for the element acting with optically defined imaging to be embodied as a ring element and to be embodied immediately adjoining the telescope in this radial direction. Therefore, this element imaging in an optically defined manner completely surrounds the telescope on the circumferential side in the circumferential direction about this optical main axis.

According to an aspect of an exemplary embodiment, the telescope is a convex-concave telescope which is embodied as a single lens system. It is oriented in such a way that a front side facing the incident light, in particular in a state of the intraocular lens where it is implanted into the eye, of this telescope has a convex curvature and a rear side facing away from the incident light of this telescope has a concave curvature. This configuration obtains a particularly advantageous magnifying effect and hence an improvement in the visual field in the case of macular degeneration. As a result of this magnification, the regions impaired by macular degeneration are virtually no longer imaged or practically displaced far to the edge of the visual field, and hence an improved eyesight impression of the patient is obtained.

Preferably, provision is made for the convexly curved front side to have a greater radius in a direction perpendicular to the optical main axis of the intraocular lens than the concavely curved rear side. As a result, the aforementioned advantages are promoted again and a specific imaging capability is obtained in the case of a very compact intraocular lens which, in particular, is very thin in the direction of the optical main axis. Hence, an implementation, which is suitable for a small incision into the eye is possible in a particularly good manner.

This configuration also means that an asymmetry is formed in respect of the lengths over which the concavely curved rear side and the convexly curved front side extend in the radial direction in relation to the optical main axis and hence perpendicular to the optical main axis.

According to an aspect of an exemplary embodiment, the telescope is entirely cavity-free and hence it is formed as a virtually solid body. As a result, firstly, the telescope has high inherent stability. Secondly, this configuration is able to avoid unwanted light ray deflections which occur on account of different media and hence on account of different refractive indices. As a result, the visual field adaptation in the case of macular degeneration may be carried out in an even more defined and precise manner.

According to another aspect of the invention, the telescope extends on both sides beyond the optically imaging or the optically effective element radially adjoining the telescope when viewed in a direction of an optical main axis of the optical part and hence also of the intraocular lens. Hence, the telescope projects beyond the optically imaging element to the front and to the back in this axial direction.

According to yet another aspect of the invention, a front side of the telescope faces the incident light to have a smaller radius than a front side of the optically imaging element and a kink is formed at a transition between the front side of the telescope and the front side of the optically imaging element. The imaging effect of the telescope may be improved by this non-flush and hence discontinuous contour profile or by arching appearing as a bulge in relation to the front side of the optically imaging element.

According to a further aspect of the invention, a concavely curved rear side of the telescope facing away from the incident light is embodied as an opening into a lateral wall of the telescope and a kink is formed at a transition of a contour profile between the lateral wall and a rear side of the optically imaging element. This also promotes the imaging property of the telescope in view of extending the visual field in the case of macular degeneration. These forms and geometries of the front side and the rear side of the telescope, which respectively project to the front and to the back in the direction of the optical main axis and which are raised, when compared with the front side and rear side of the directly adjoining optically imaging element, are advantageous since this also enables a very lateral incidence of light and/or an oblique incidence of light into the telescope.

The desired imaging properties, which are also different in that case, of the separate components are amplified and the precision for the visual field adaptation in the case of macular degeneration is improved by the specific transitions, respectively provided with a kink, or the boundaries, formed thereby, of the front and sides and the rear sides of the telescope on the one hand and of the element with the optically imaging effect on the other hand.

Preferably, the optically imaging element is a monofocal lens. In particular, the optically imaging element is a ring lens.

According to an aspect of an exemplary embodiment, the intraocular lens has a magnification factor of at least 1.35, in particular greater than 1.5, through the telescope. Such relatively large magnification values substantially promote the visual field adaptation in the case of macular degeneration.

In addition, or instead of this, provision can be made for the intraocular lens, in particular the telescope, to have a central thickness of less than 2 mm as measured along the optical main axis of the intraocular lens. Such a thin configuration of the intraocular lens, in particular in the optical part on the optical main axis, substantially promotes an implantation, which is suitable for a small incision, into an eye. Such a flat intraocular lens can be folded to be very small and therefore can be introduced into the eye through a relatively small incision in the eye.

According to an aspect of the invention, the material of the optical element and of the telescope has a refractive index of greater than 1.45.

According to an aspect of an exemplary embodiment, a magnification or magnification factor of at least 1.6 is achieved with, at the same time, a central thickness of at most 2 mm, in particular by the specific geometry of the telescope and of the optically imaging element, for example with a refractive index value of 1.46. The same magnification factor can be achieved with a higher refractive index value in the case of a reduced central thickness. An increase in the magnification factor can be achieved in the case of the same central thickness by way of a higher refractive index of the material of the telescope and of the optically effective element. Accordingly, a reduction in the central thickness in the case of the same magnification factor can be achieved by increasing the refractive index value of the material of the telescope and of the optically effective element. Preferably, the intraocular lens is embodied such that, in the case of the refractive index value of 1.58, the central thickness is reduced by at least 45 percent with, however, the same magnification factor in comparison with a configuration with a material having a refractive index value of 1.46.

Peripheral vision with the intraocular lens is also facilitated by the additional optically imaging element, in particular in the form of a ring surrounding the telescope radially to the outside and on the circumferential side. This additional peripheral vision is also particularly advantageous for patients with macular degeneration, also in view of imaging the entire visual field.

According to an aspect of an exemplary embodiment, a diffractive structure is embodied on a front side of the telescope facing the incident light in the case of light incident on the intraocular lens. Additionally, or instead, a diffractive structure is embodied on a rear side of the telescope facing away from the incident light. By way of example, a diffractive structure may be formed by Fresnel zones. Such diffractive structures obtain a reduction in the central thickness of the optical part in a particularly advantageous manner since the telescope too may be embodied to be smaller in terms of its extent in the direction of the optical main axis. According to another aspect of the invention, such a diffractive structure also extends the functionality of the intraocular lens to the extent that it is also a depth of field lens and thereby increases the depth of field. Such an intraocular lens facilitates an improved visual field adaptation, precisely for patients with macular degeneration, by way of the magnification effect of the telescope and at the same time improves sharp imaging over a larger range by increasing the depth of field.

According to an aspect of the invention, the optically imaging element is designed in such a way that it has a refractive power of between 15 and 25 diopters, preferably between 17 and 22 diopters, in particular 20 diopters.

According to a further aspect of an exemplary embodiment, a front side and/or a rear side of the optically imaging element is not a continuous spherical or aspherical surface but for at least one step is embodied in the respective surface profile. In particular, it is thus also possible for a diffractive structure to be embodied on the optically imaging element. Specifically, if diffractive structures are embodied both on the front side and/or the rear side of the optically imaging element and on the front side and/or the rear side of the telescope, the diffractive structures have different embodiments in view of their number of diffractive elements, in particular in the form of Fresnel zones, and/or in view of the geometric configurations of these diffractive zones.

Light beams incident in spherical waves may be converted into exactly plane waves, or vice versa, by way of the intraocular lens according to an aspect of the invention or an advantageous configuration thereof. It is also possible to exactly convert spherical waves, whether they be convergent or divergent, into other exact spherical waves, which may also be convergent or divergent. The diameters of incident light beams may be modified by the intraocular lens. A wave, e.g., a plane wave, incident at the front surface or at the front side and converted into a convergent spherical wave by the telescope and this convergent spherical wave may, once again, be converted into a plane wave at the rear side of the telescope. The diameter of the resultant converted plane wave then always is smaller in this case than the diameter of the incident plane wave.

Further features of the exemplary embodiments of the invention emerge from the claims, the figures and the description of the figures. The features and feature combinations mentioned in the description above and the features and feature combinations mentioned in the description of the figures and/or only shown in the figures may be used not only in the respectively specified combination, but also in other combinations or on their own, without departing from the scope of the invention. Hence, exemplary embodiments of the invention which are not explicitly shown and explained in the figures but which emerge from the explained exemplary embodiments by way of separate feature combinations and which are producible should therefore also be considered to be included and disclosed. Therefore, exemplary embodiments and feature combinations which do not have all features of an originally phrased independent claim should also be considered to be disclosed.

BRIEF DESCRIPTION OF THE DRAWINGS

The invention will now be described with reference to the drawings wherein.

DESCRIPTION OF EXEMPLARY EMBODIMENTS

In the figures, equivalent or functionally equivalent elements are provided with the same reference numerals.

Figure 1A:
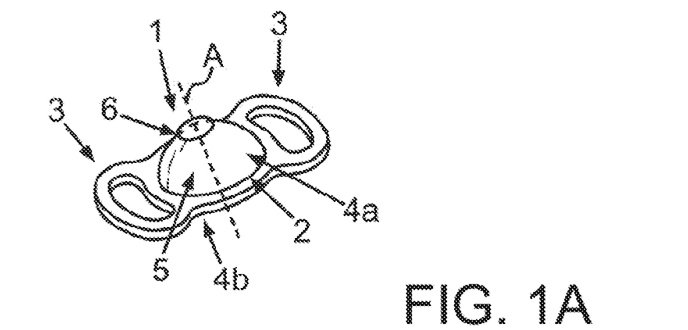
FIG. 1A shows a perspective illustration of a first exemplary embodiment of an eye lens according to the invention.

FIG. 1A shows a first exemplary embodiment of an intraocular lens 1 in a perspective illustration. The intraocular lens 1 includes an optical part 2 and, adjoining it, an optically ineffective haptic part 3, or haptics, which is only embodied to hold the intraocular lens 1 in the eye. The intraocular lens 1 is foldable and may be introduced into an eye through a small incision. The optical part 2, which defines the optical imaging property of the intraocular lens 1, includes an optical main axis A, which is perpendicular to the optical part 2. Moreover, when viewed in the direction of this optical main axis A, the optical part 2 includes a first optical area or side 4a, which may be a front side, and, opposite thereto, a second optical area or side 4b, which may be a rear side. In the implanted state of the intraocular lens 1 in the eye, the first optical side 4a faces the cornea, whereas the second optical side 4b faces away from the cornea.

Figure 1B:
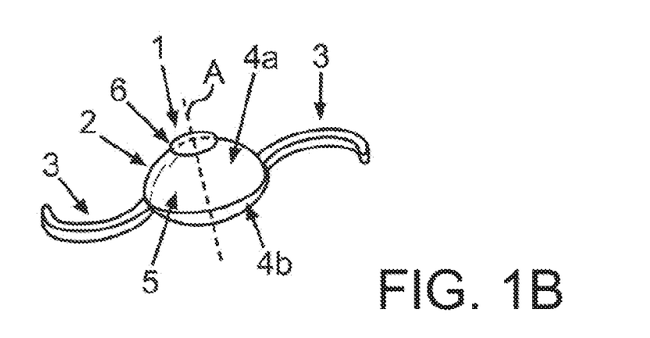
FIG. 1B shows a perspective illustration of a further exemplary embodiment of an eye lens according to the invention.

FIG. 1B shows a further exemplary embodiment of an intraocular lens 1 in a perspective illustration. It differs from the exemplary embodiment shown in FIG. 1A by different haptics 3. The intraocular lens 1 is held in the eye by the haptics 3. In principle, provision may also be made of differently shaped and configured haptics 3.

As may be identified schematically in the illustrations in FIGS. 1A and 1B, the intraocular lenses 1 each have a specifically embodied optical part 2. In this context, the respective optical part 2 includes, in particular, an optically imaging element 5 and a telescope 6 in each case. The complete or entire telescope 6 respectively has an integral embodiment, and hence it is embodied as a single part, in FIGS. 1A and 1B. Moreover, this telescope 6 is integrated into the optically imaging element 5 and therefore also has an integral embodiment with the optically imaging element 5 and, in particular, it is also produced in integral fashion therewith. This means that the telescope 6 is embodied in a common production process together with the optically imaging element 5.

In this context, the integral optical part 2 may be made from a polymer material.

Figure 2:
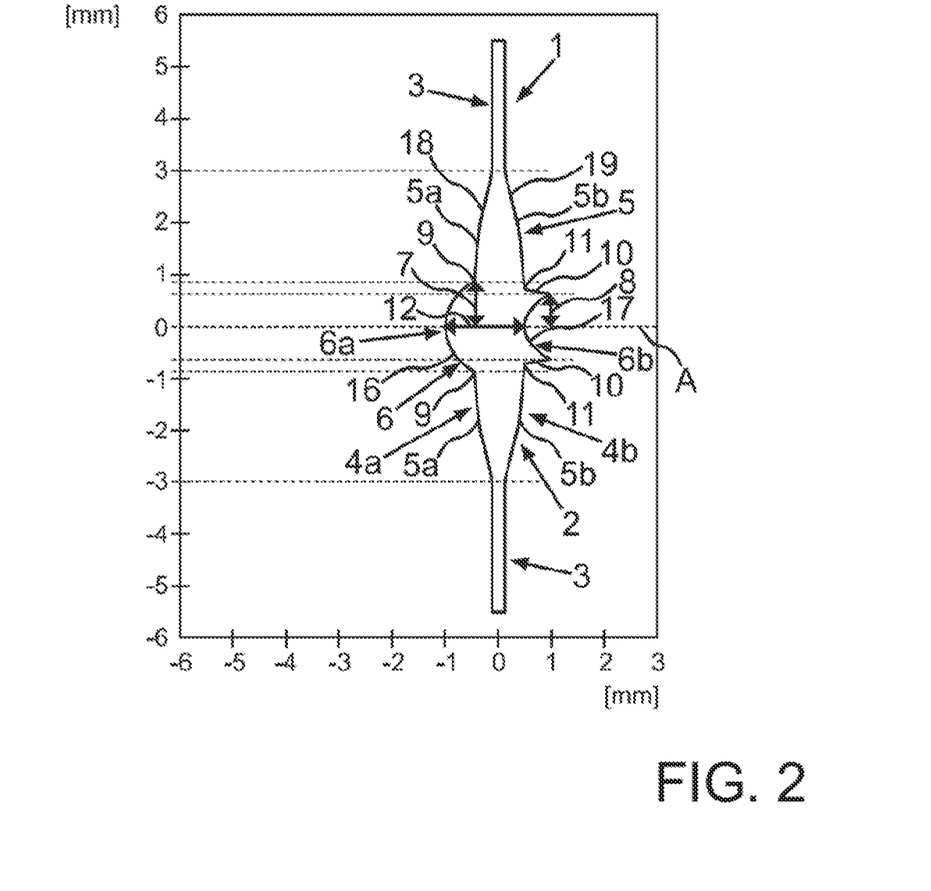
FIG. 2 shows a vertical sectional illustration through the first exemplary embodiment of an intraocular lens according to the invention.

FIG. 2 shows the first exemplary embodiment of the intraocular lens 1 in a schematic vertical sectional illustration and hence in a sectional plane containing the optical main axis A and extending through the haptics 3 and the optical part 2. The exemplary dimensional specifications may also be embodied differently but provide relative values in view of the relative sizes of individual parts of the intraocular lens 1 and, in particular, of the individual parts of the optical part 2.

In the illustration of FIG. 2, it is possible to identify that the telescope 6 is a Galilean telescope. The integral telescope 6 is embodied symmetrically about the main axis A and sits centrally in the middle in the optical part 2. As viewed in a direction perpendicular to the main axis A and hence in the radial direction in relation to the main axis A, this is then followed by the optically imaging element 5, which is embodied as a ring and which surrounds the telescope 6 in a circumferential manner about the main axis A.

In the shown exemplary embodiment, the optical side 4a represents a front side, meaning that this optical side 4a faces the cornea in the implanted state of the intraocular lens 1 in the eye, in particular in the capsular bag. By contrast, the optical second side 4b then faces away from the cornea in the exemplary embodiment.

In the exemplary embodiment, the optically imaging element 5 is a monofocal lens with a biconvex embodiment. To this end, a front side 5a facing towards the cornea in the implanted state or facing the incident light has convex curvature, and a rear side 5b, facing away from the incident light, of this optically imaging element 5 likewise has convex curvature. In an exemplary embodiment, the optically imaging element 5 preferably has a refractive power of 20 diopters, for example.

As may also be seen in FIG. 2, the telescope 6 is embodied as a solid component and hence embodied without a cavity. Hence, the entire body of the telescope 6 is filled with the polymer material. The telescope 6 is a single lens system.

As may be recognized, the telescope 6 represents a convex-concave telescope. In this context, a front side 6a facing the incident light and therefore also facing the cornea in the implanted state in the eye has a convexly curved embodiment, in particular a completely convexly curved embodiment. A rear side 6b, facing away from the incident light and therefore also facing away from the cornea in the implanted state of the intraocular lens 1, of the telescope 6 has concave curvature, in particular, a completely concave curvature.

As may furthermore be seen in FIG. 2, the convexly curved front side 6a has a greater radius 7 in a direction perpendicular to the main axis A than the curved rear side 6b, when considered in this direction, which has a smaller radius 8 in this context. Hence, the telescope 6 has a tapering embodiment when considered from the front side 6a thereof to the rear side 6b thereof—along the main axis A. It therefore represents a cone-like shape, wherein this cone then has the specifically convexly shaped front side 6a and the specifically concavely shaped rear side 6b. As may moreover be identified, the curvature of the front side 6a is different from, in particular smaller than, the curvature of the rear side 6b since a radius 16 of the front side is greater than a radius 17 of the rear side 6b.

It is furthermore possible to identify that the radius 16 of the convex form of the front side 6a is less than a radius 18 of the convex form of the front side 5a of the optically imaging element 5 and a radius 19 of the rear side 5b. Therefore, a clear transition, which is realized by a kink 9, is embodied between the telescope 6 and the optically imaging element 5. The telescope 6 arches in a raised fashion to the front or to the outside in relation to the convex arching of the front side 5a of the optically imaging element 5 at this front first side 4a of the optical part 2. Therefore, when viewed in the direction of the optical main axis A, the telescope 6 extends beyond the optically imaging element 5 toward the front with its entire dimension in the direction perpendicular to the main axis A. This means that the front side 6a, which starts at the kink 9 with an edge or an end, then already extends further forward from this edge or this end than the point of the front side 5*a* lying furthest to the front in this respect when viewed in the direction of the main axis A.

When viewed along the main axis A, the exemplary embodiment also provides for the telescope 6 to have a raised embodiment toward the rear in relation to the convexly curved rear side 5*b* and for it to extend further to the outside or to the back. Here too, a kink 11 is formed at a confluence or coming together of the rear side 5*b* and a lateral wall 10 of the telescope 6. The lateral wall 10 is optically inactive. The concavely curved rear side 6*b* only opens into the lateral wall 10 and is only connected to the rear side 5*b* by the lateral wall 10.

In particular, the telescope 6 may be provided in an exemplary embodiment that has a magnification factor of at least 1.35, in particular greater than 1.5, and a central thickness 12 of the optical part 2, in particular of the telescope 6, being less than or equal to 2 mm as measured along the optical main axis A and the material of the optical part 2 having a refractive index of at least 1.45 or more.

Figure 3:
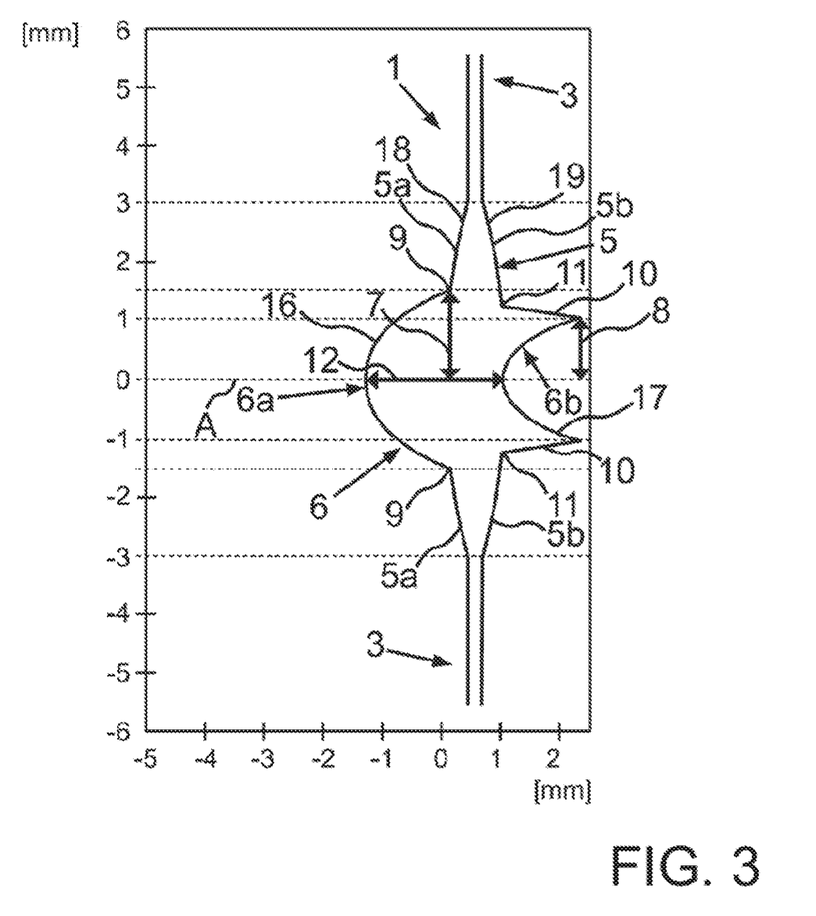
FIG. 3 shows a vertical sectional illustration through a second exemplary embodiment of an intraocular lens according to the invention.

FIG. 3 shows a further exemplary embodiment of an intraocular lens 1 in a further vertical sectional illustration. In contrast to the illustration in FIG. 2, the intraocular lens 1 only has different dimensions of the telescope 6 in comparison with the element 5.

Figure 4:
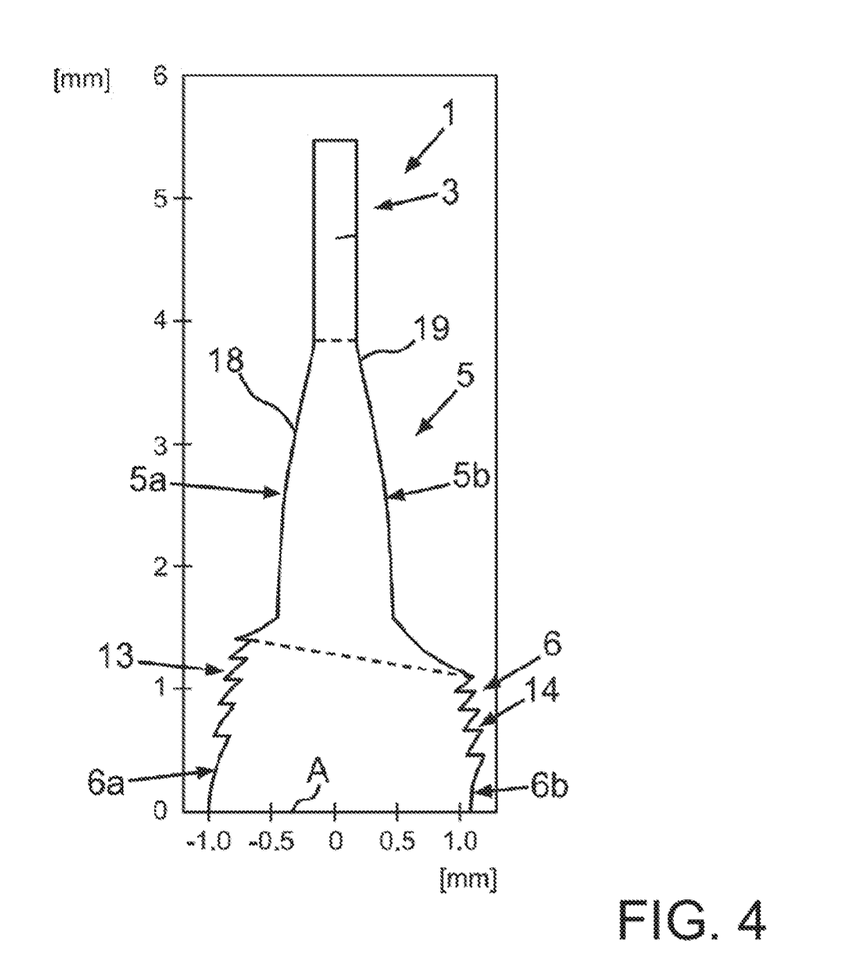
FIG. 4 shows a vertical sectional illustration through a third exemplary embodiment of an intraocular lens according to the invention.

FIG. 4 shows another exemplary embodiment of an intraocular lens 1 in a further vertical sectional illustration, with only an upper part above the optical main axis A being illustrated in this case. As can be seen here, a diffractive structure 13 is applied in regions onto the surface of the convexly curved front side 6*a*, said diffractive structure being a plurality of Fresnel zones in the exemplary embodiment. Moreover, the exemplary embodiment provides for a further diffractive structure 14 also to be applied onto the concavely curved rear side 6*b* of the telescope 6, at least in part onto this concavely curved surface, said further diffractive structure preferably likewise being formed by a plurality of Fresnel zones.

Provision may also be made for a diffractive structure 13 or 14 to be respectively applied only onto the front side 6*a* or only onto the rear side 6*b*. The diffractive structures 13 and/or 14 are formed in an outer region of the telescope 6 adjoining the optically imaging element 5 in the radial direction and are therefore only formed in regions on the front side 6*a* and/or the rear side 6*b* in the exemplary embodiment.

In particular, provision can be made for the diffractive structures 13 and 14 to be different. This means that the number of the diffractive zones may be different and/or the geometric configurations of the diffractive zones may be different.

The illustration in FIG. 4 also, in turn, specifies a scaling in the vertical direction and horizontal direction, and, here too, the values should be understood to be true to scale, in particular in view of the dimensional relationships of the individual parts of the intraocular lens 1.

Figure 5:
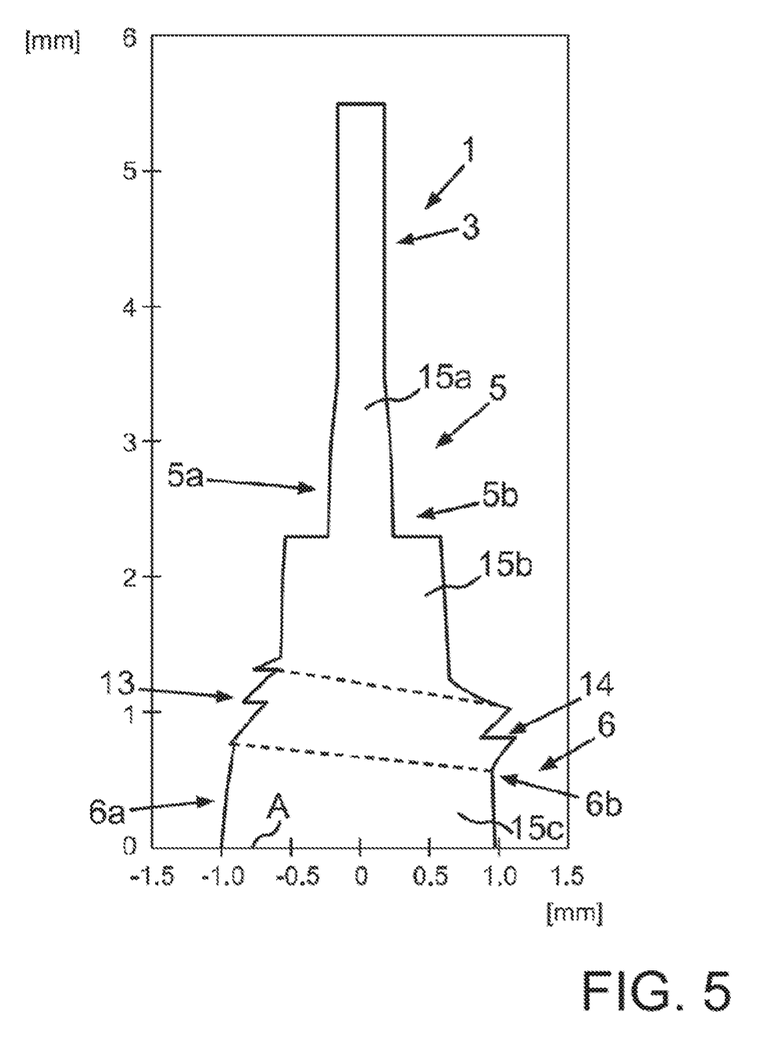
FIG. 5 shows a vertical sectional illustration through a fourth exemplary embodiment of an intraocular lens according to the invention.

FIG. 5 shows a further example embodiment of an intraocular lens 1 in a vertical sectional illustration, with only an illustration above an optical main axis A being shown here in a manner corresponding to FIG. 4. In this embodiment, provision is made for the front side 5*a* and also the rear side 5*b* of the optically imaging element 5, respectively, to have a diffractive structure and to have a stepped exemplary embodiment in this context and therefore not to have a continuous convex shape.

Provision may also be made for only the front side 5*a* or only the rear side 5*b* to have such a diffractive structure.

Monofocal regions 15*a*, 15*b*, and 15*c* are formed by this exemplary embodiment.

It is understood that the foregoing description is that of the exemplary embodiments of the invention and that various changes and modifications may be made thereto without departing from the spirit and scope of the invention as defined in the appended claims.

What is claimed is:

1. An intraocular lens comprising:
an optical part including an optically imaging element and a convex-concave telescope; and
a haptic part connected to the optical part;
the convex-concave telescope being formed in one piece, being integrated into the optically imaging element, having a convexly-curved front side and a concavely-curved rear side, being arranged as a single lens, and being a solid cavity-free arrangement;
the convexly-curved front side of the convex-concave telescope having a convex curvature for facing towards incident light entering the intraocular lens;
the concavely-curved rear side of the convex-concave telescope having a concave curvature for facing away from the incident light;
the convexly-curved front side of the convex-concave telescope having a first radius;
the concavely-curved rear side of the convex-concave telescope having a second radius; and
the first radius being larger than the second radius,
wherein the optical part of the intraocular lens defines an optical main axis,
wherein the optically imaging element radially adjoins the convex-concave telescope, and
wherein the convex-concave telescope extends on both sides of the intraocular lens beyond the optically imaging element when viewed in a direction of the optical main axis of the optical part.

2. The intraocular lens of claim 1, wherein:
the optical part of the intraocular lens defines an optical main axis,
the first radius is defined in a direction perpendicular to the optical main axis of the intraocular lens, and
the second radius is defined in the direction perpendicular to the optical main axis of the intraocular lens.

3. An intraocular lens comprising:
an optical part including an optically imaging element and a convex-concave telescope; and
a haptic part connected to the optical part;
the convex-concave telescope being formed in one piece, being integrated into the optically imaging element, having a convexly-curved front side and a concavely-curved rear side, being arranged as a single lens, and being a solid cavity-free arrangement;
the convexly-curved front side of the convex-concave telescope having a convex curvature for facing towards incident light entering the intraocular lens;
the concavely-curved rear side of the convex-concave telescope having a concave curvature for facing away from the incident light;
the convexly-curved front side of the convex-concave telescope having a first radius;
the concavely-curved rear side of the convex-concave telescope having a second radius;
the first radius being larger than the second radius; and
a kink, wherein:
the convexly-curved front side of the convex-concave telescope facing towards the incident light entering the intraocular lens has a first radius, the optically imaging element has a front side,
the front side of the optically imaging element has a second radius,
the first radius is smaller than the second radius, and
the kink is formed at a contour transition between the convexly-curved front side of the convex-concave telescope and the front side of the optically imaging element.

4. The intraocular lens of claim 1, further comprising:
a kink, wherein:
the convex-concave telescope has a lateral wall,
the optically imaging element has a rear side,
the concavely-curved rear side of the convex-concave telescope facing away from the incident light entering the intraocular lens opens into the lateral wall of the convex-concave telescope, and
the kink is formed at a contour transition between the lateral wall and the rear side of the optically imaging element.

5. The intraocular lens of claim 1, wherein the optically imaging element is a monofocal lens.

6. The intraocular lens of claim 1, wherein the optically imaging element is a monofocal ring lens.

7. The intraocular lens of claim 1, wherein:
the optical part of the intraocular lens defines an optical main axis, and
a central thickness of the intraocular lens as measured along the optical main axis is less than 2 mm.

8. The intraocular lens of claim 1, wherein:
the optical part of the intraocular lens defines an optical main axis, and
a central thickness of the convex-concave telescope as measured along the optical main axis is less than 2 mm.

9. The intraocular lens of claim 1, further comprising:
at least one of a first diffractive structure arranged on the convexly-curved front side of the convex-concave telescope facing towards the incident light entering the intraocular lens and a second diffractive structure arranged on the concavely-curved rear side of the convex-concave telescope facing away from the incident light.

* * * * *